Figure 1:
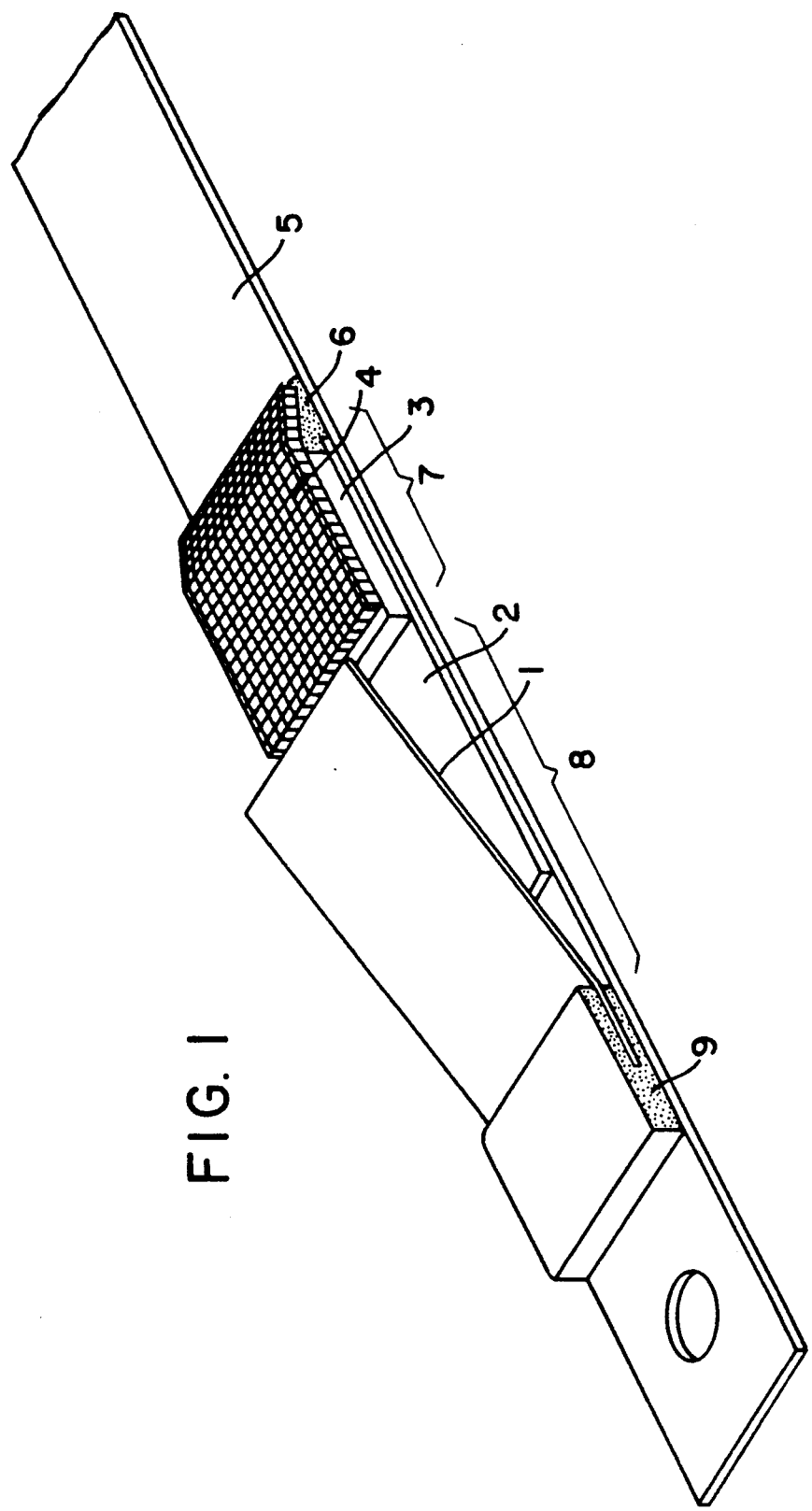

United States Patent [19]
Wilk et al.

[11] Patent Number: 5,262,067
[45] Date of Patent: Nov. 16, 1993

[54] DEVICE AND ITS USE FOR THE SEPARATION OF PLASMA FROM WHOLE BLOOD

[75] Inventors: Hans-Erich Wilk, Einhausen; Peter Vogel, Hemsbach; Rolf Lerch, Ilvesheim; Erich Schneider; Andreas Marschall, both of Mannheim, all of Fed. Rep. of Germany

[73] Assignee: Boehringer Mannheim GmbH, Mannheim, Fed. Rep. of Germany

[21] Appl. No.: 698,461

[22] Filed: May 10, 1991

[30] Foreign Application Priority Data

May 15, 1990 [DE] Fed. Rep. of Germany ....... 4015589

[51] Int. Cl.$^5$ ...................... B06D 15/00; G01N 33/52
[52] U.S. Cl. .................................. 210/767; 210/732; 210/506; 210/508; 422/56; 422/73; 422/101; 436/177
[58] Field of Search .............. 210/767, 729, 732, 506, 210/508, 509; 422/56, 73, 101; 435/2; 436/177

[56] References Cited

U.S. PATENT DOCUMENTS

| | | |
|---|---|---|
| 3,146,163 | 8/1964 | Brewer. |
| 4,477,575 | 10/1984 | Vogel et al. .............. 210/767 |
| 4,753,776 | 6/1988 | Hillman et al. ............ 422/101 |
| 4,780,280 | 10/1988 | Berger et al. .............. 422/56 |
| 4,788,152 | 11/1988 | Doeding et al. ............ 436/69 |
| 4,816,224 | 3/1989 | Vogel et al. .............. 210/767 |
| 4,910,150 | 3/1990 | Doeding et al. ............ 422/56 |
| 4,933,092 | 6/1990 | Aunet et al. .............. 210/732 |
| 5,055,195 | 10/1991 | Trasch et al. ............. 210/638 |

FOREIGN PATENT DOCUMENTS

| | | |
|---|---|---|
| 045476 | 2/1982 | European Pat. Off.. |
| 057110 | 8/1982 | European Pat. Off.. |
| 133895 | 3/1985 | European Pat. Off.. |
| 94502 | 9/1986 | European Pat. Off.. |
| 0239002 | 3/1987 | European Pat. Off.. |
| 0269240 | 6/1988 | European Pat. Off.. |
| 0305803 | 8/1988 | European Pat. Off.. |
| 295526 | 12/1988 | European Pat. Off.. |
| 0325413 | 7/1989 | European Pat. Off.. |
| 353570 | 2/1990 | European Pat. Off.. |
| 1498577 | 4/1969 | Fed. Rep. of Germany. |
| 3441149 | 5/1986 | Fed. Rep. of Germany. |
| 3540526 | 5/1987 | Fed. Rep. of Germany ........ 422/56 |

*Primary Examiner*—Robert A. Dawson
*Assistant Examiner*—Sun Uk Kim
*Attorney, Agent, or Firm*—Felfe & Lynch

[57] ABSTRACT

The invention concerns a device and its use for separating plasma from whole blood by means of a fibre-containing layer which contains an erythrocyte-aggregating substance and is characterized in that the fibre-containing layer contains glass fibres which are coated with polyvinyl alcohol or with polyvinyl alcohol/polyvinyl acetate. The invention also concerns a test carrier for the determination of a blood component as well as a process for separation from whole blood in which the device according to the present invention is used.

15 Claims, 2 Drawing Sheets

DEVICE AND ITS USE FOR THE SEPARATION OF PLASMA FROM WHOLE BLOOD

The invention concerns a device and its use for separating plasma from whole blood with a fibre-containing layer which also contains a substance which aggregates erythrocytes. Furthermore the invention concerns a process for separating plasma from whole blood in which whole blood comes into contact with an erythrocyte-aggregating substance and erythrocytes are held back by a fibre-containing layer. In addition the invention concerns a test carrier for the determination of a blood component containing a zone for the isolation of plasma and a test zone. Finally the invention concerns the use of glass fibres coated with polyvinyl alcohol or polyvinyl alcohol/polyvinyl acetate.

Erythrocytes often interfere in clinical-chemical examinations of whole blood because of their inherent colour, in particular in colorimetric tests. Plasma and serum which are obtained from whole blood are the most important sample material for the analysis of dissolved blood components. Centrifugation is usually used for separating serum or plasma from whole blood. However, this is a problem, in particular when using small sample volumes; in addition the separation of supernatant from the so-called blood clot which is sedimented by the centrifugation is not always easy.

The use of whole blood is particularly difficult in rapid diagnostics. Rapid diagnostics consist of absorptive materials or of materials capable of swelling which contain reagents and are brought as such into contact, e.g. as a paper impregnated with reagents or present on a solid carrier, with the substance to be examined whereby as a result of the usually very short reaction a measurable change of the original rapid diagnostic takes place e.g. preferably a change in colour which can either be evaluated visually or which can be measured by reflectance photometry. Turbid or coloured solutions such as blood can significantly interfere with the reading. Many attempts have therefore been made to provide devices and to develop processes which can be used to separate plasma from whole blood in particular for rapid diagnostics.

A device is described in EP-B-0057 110 among others for the analysis of whole blood. In this process an agent which agglutinates red blood cells is used which is immobilized on an essentially non-wettable material. Beads are preferably used as the carrier. Polyacrylamide is the preferred material for this.

In U.S. Pat. No. 3,146,163 and DE-A-14 98 577 whole blood is applied to a material coated with a haemagglutinin, such as phytohaemagglutinin, for the separation of plasma. Plastics and fibrous materials such as cardboard are mentioned as possible carrier materials.

A process for the separation of whole blood is described in DE-A-34 41 149 which consists of applying whole blood onto a matrix impregnated with lectin and in doing so plasma or serum are isolated. The matrix consists of absorptive material with a relative resistance to fluid flow of up to 40%. Materials are useful for this which have a fabric structure or fibre structure and a resistance to fluid, flow which is as small as possible. Cotton and viscose fabrics and cellulose materials are mentioned as preferred materials. A clear disadvantage of this process is, however, that the separated plasma or serum has to be washed out of the matrix with a diluting agent.

A further device for separating plasma or serum from whole blood is described in EP-A-0 295 526. The device contains an absorptive matrix which is treated with an agent which agglutinates blood cells. Thrombin or lectin are mentioned as the agent which agglutinates blood cells. Hydrophilic powders, sponge-like and clay-like materials, fabrics and polymers are recommended as the absorptive matrix. Fibre-containing papers are also understood as polymers. Filter paper is the preferred matrix.

The subject matter of EP-A-0 194 502 is an agent for separating plasma or serum from whole blood in which an absorptive matrix impregnated with lectin is used as the separating layer. The matrix preferably consists of textile fabrics or a cellulose-containing material.

In EP-A-0 325 413 polyvalent cations are immobilized on an absorptive solid material such that a cationic surface is formed onto which erythrocytes are bound when contacted with whole blood. The preferred carrier material is paper.

In EP-A-0 133 895 an absorptive porous material impregnated with substances with several polar groups is used to separate plasma from whole blood. Papers, pads and fabrics are generally mentioned inter alia as examples.

In EP-A-0 305 803 a device for separating blood cells from erythrocyte-containing body fluids is described which consists of a fibre-containing filter layer containing erythrocyte-agglutinating antibodies and, if desired, a lectin or it consists of a filter layer of glass fibres and a lectin.

The subject matter of EP-A-0 269 240 is a device for separating plasma from red blood cells in which the whole blood is contacted with a filter which consists of glass fibres which can carry an erythrocyte-agglutinating agent.

Of the methods for separating whole blood known from the state of the art, those which have proven to be of most practical interest are those in which whole blood is contacted with an erythrocyte-aggregating substance and the erythrocytes are retained by a fibre-containing layer. A common drawback of such erythrocyte-separation layers is, however, that the erythrocytes are only satisfactorily separated when using diluted samples and/or that haemolysis occurs when the erythrocytes to be separated are contacted with the separating layer. If the erythrocytes in a whole blood sample have to be first diluted before separation, this requires an additional step which is tedious and can subsequently falsify the results of the measurements carried out. A dilution step is therefore undesirable in practice.

Haemolysis leads to the release of haemoglobin from the erythrocytes and thus to a discolouration of the plasma or serum. Such discolourations can considerably interfere with colorimetric tests. In addition other erythrocyte constituents are released into the plasma in haemolysis. Even if the resulting discolouration by haemoglobin does not lead to an interference of a colorimetric test, the determination of certain parameters can be considerably falsified by even slight haemolysis. For example potassium ions are released from erythrocytes on haemolysis so that as a result the determination of potassium in plasma can be completely erroneous. Thus, e.g. EP-A-0 045 476, teaches agents and processes which are used for separating plasma or serum from whole blood with glass fibre layers which can be used for a good separation of erythrocytes from undiluted whole blood. However, the slight haemolysis of erythrocytes caused by the glass can be sufficient to falsify a determination of potassium from whole blood.

The object of the present invention is therefore to provide a means for separating the cellular components, in particular erythrocytes, of undiluted blood from plasma and to cause less haemolysis in this separation. The separation should in particular also be possible on rapid diagnostics.

The invention provides a device for separating plasma from whole blood with a fibre-containing layer which contains an erythrocyte-aggregating substance and in which the glass fibres of this layer are coated with polyvinyl alcohol or with polyvinyl alcohol/polyvinyl acetate.

The invention also provides a process for separating plasma from whole blood in which the whole blood is brought into contact with an erythrocyte-aggregating substance and the erythrocytes are retained during passage through a glass fibre-containing layer in which the glass fibres are coated with polyvinyl alcohol or polyvinyl alcohol/polyvinyl acetate.

In addition the invention provides a test carrier for the determination of a component of blood containing a zone for isolating plasma and a test zone which is characterized in that the zone for isolating plasma contains a device which comprises a glass fibre-containing layer which carries an erythrocyte-aggregating substance in which the glass fibres of this layer are coated with polyvinyl alcohol or polyvinyl alcohol/polyvinyl acetate.

Finally a subject matter of the invention is the use of glass fibres coated with polyvinyl alcohol or polyvinyl alcohol/polyvinyl acetate which carry a substance which leads to the aggregation of erythrocytes for the separation of plasma from whole blood.

Surprisingly it was found according to the present invention that a glass fibre layer, in which the glass fibres are coated with polyvinyl alcohol or polyvinyl alcohol/polyvinyl acetate and carry a substance which leads to the aggregation of erythrocytes, is suitable for very good separation of the cellular components of undiluted blood from plasma without the occurrence of substantial haemolysis in this process.

Although glass fibres coated with polyvinyl alcohol or polyvinyl alcohol/polyvinyl acetate and layers containing such fibres are known from EP-A-0 239 002, in this patent this coating merely serves to make the fibres neutral to coagulation. This document does not infer that a coating of polyvinyl alcohol/polyvinyl acetate can have an influence which suppresses haemolysis. Moreover no erythrocyte-aggregating substances are mentioned.

In EP-A-0 353 570 an impregnated carrier matrix which is detachable with reagent is also described which consists of glass coated with polyvinyl alcohol. The carrier matrix is not used for separating plasma from blood. The fact that coated glass can carry erythrocyte-aggregating substances is not taught in this document. Also, haemolysis is not discussed.

Glass fibres of different diameters can be used for the present invention. The glass fibre material can consist of alkaline-containing or alkaline-free borosilicate glass or even of pure quartz glass. Fibre materials of other technical glasses e.g. boron-free alkaline glasses, crystal glass, lead glass and others are not commercially available in the necessary fibre size and could not therefore be examined. There is no reason to suggest that they are not also suitable. The average diameter of the glass fibres can be between 0.5 $\mu$m and 2.5 $\mu$m, in particular between 0.5 $\mu$m and 1.5 $\mu$m. The fibre diameters can vary widely depending on their manufacture, they should, however, only exceed an upper limit of 10 $\mu$m in exeptional cases. Their length is only limited by the type of stacking but it has otherwise no influence. Depending on the type of stacking, densities of 0.1–0.5, usually 0.2–0.4 g/cm$^3$ have been found to be advantageous. The glass fibres can be used in a loosely stacked form as well as in the form of papers, pads or felts and also in any desired shape by being held by an outer form.

Polyvinyl alcohol is usually produced from polyvinyl acetate by saponification in which complete or partial saponification is carried out depending on the desired properties of the product. For the purpose of the present invention a complete as well as a partially saponified product can be used. Polyvinyl alcohols which are commercially available in large amounts differ especially in their average molecular weight which is usually between 10000 and 100000 and in some special cases even much higher values can also be attained, as well as in the residual content of acetyl groups. The low molecular weight compounds which contain ca. 5–15%, in particular about 10% of acetyl groups are the most readily soluble in water. High molecular weight products and/or products which contain more acetyl, in contrast, are less soluble in water. In addition the interaction between the polyvinyl alcohol chains has an influence on the solubility. As a result of a parallel arrangement of the polymer chains in particular regions, "crystalline" zones are formed whereby the tendency for parallel orientation of the chains is the greater the more uniform the chains are and the smaller their proportion of acetyl groups is because acetyl groups counteract an orientation to the greatest extent. As a consequence the "crystallinity" increases particularly substantially at a saponification degree of 97–100 mol%, i.e. at an acetylation degree of 0–3 mol% whereby in contrast the solubility in cold water is greatly decreased.

The water solubility can in addition be reduced by post-treatment with aldehydes (acetalization) or by other chemical conversion of the alcohol groups. In particular those polyvinyl alcohols which have a very slight solubility in cold water can be used according to the present invention. The products should dissolve only slowly in water or not dissolve at all at 20° C. At temperatures of 50°–100° C., in particular temperatures of over 60° C. solubility in water is, however, not disadvantageous.

According to the present invention the glass fibres used for separating plasma from whole blood are coated with a polyvinyl alcohol or polyvinyl alcohol/polyvinyl acetate layer in such a way that the whole glass surface is covered. Even relatively small amounts in particular about 0.5–20% by weight, preferably 1–10% by weight polyvinyl alcohol or polyvinyl alcohol/polyvinyl acetate in relation to the glass fibres is sufficient for this.

All substances are basically suitable for coating polyvinyl alcohol or polyvinyl alcohol/polyvinyl acetate coated glass fibres according to the present invention with erythrocyte-aggregating substances which, in concentrations which do not lead to a significant haemolysis and independent of blood groups, are able to aggregate erythrocytes to large conglomerations in such a way that they can be separated out of the blood by the fibre layer. Cationic polymers, lectins, antibodies against erythrocytes or mixtures of individual substances or all of these substances are preferably used for this.

All organic or inorganic polymers which have more than 10 positive charges per molecule, preferably more than 20 are in principle suitable as the cationic polymer. Copolymers of N,N,N',N'-tetramethyl-1,6-hexanediamine and 1,3-dibromopropane (Polybren ®), polyethylenimine (Polymin ®) and polypiperidinium salt, for example polydimethylpiperidinium chloride have proven to be particularly preferable. Especially preferred is Polybren ®, in particular that which has a molecular weight of less than 6000.

Lectins which can be used are above all those which are able to bind to all human erythrocytes and thus agglutinate them i.e. they should not be blood-group specific. The lectins of Solanum tuberosum (potato), Lycopesicon esculantum (tomato), Ricinus communis or of Phytolacca americana (kermes berry) are preferably each used individually, or as a combination of several or all of the aforementioned.

Antibodies which can be used according to the present invention bind to surface structures of erythrocytes. The antibodies should preferably be blood-group unspecific otherwise the antibodies have to be matched to the blood sample present. Monoclonal or polyclonal antibodies can be used whereby the use of polyclonal antibodies which are more "simple" to produce is adequate.

According to the present invention glass fibre pads have proven to be especially advantageous as the device for separating plasma from whole blood. The production of a glass fibre pad according to the present invention can take place by additionally treating an appropriate glass fibre pad with a solution of polyvinyl alcohol in water or with a suitable organic solvent and subsequently drying it, preferably at temperatures of over 60° C., especially at 90°–140° C., or by adding polyvinyl alcohol or polyvinyl alcohol/polyvinyl acetate during the production of the glass fibre pad. Glass fibre pads are produced in such a way that the dry and matted glass fibres which have an average diameter of 0.5–2.5 $\mu$m, in particular of 0.5 and 1.5 $\mu$m, are suspended in a very large excess of water, separated by this means and this "vat" is formed into thin layers analogous to the usual methods in paper production and with the aid of the usual machines for this and dried. The polyvinyl alcohol powders or fibres added to the vat become uniformly dispersed in the mixture when the glass fibres are suspended and in the subsequent production of the pad they are dissolved or melted to such an extent that they form a uniform coating on the glass fibres during the subsequent drying of the pad.

In order to apply the erythrocyte-aggregating substance onto a glass fibre-containing layer, the latter is preferably impregnated with a solution of the appropriate substance in which e.g. the impregnation solution is applied to the glass fibre layer or this is immersed in the impregnation solution.

A glass fibre pad whose glass fibres are coated with polyvinyl alcohol or polyvinyl alcohol/polyvinyl acetate has an increased wet strength compared to untreated glass fibre pads. While untreated glass fibre pads, in particular in amounts and sizes necessary for technical and larger-scale production, cannot be immersed in impregnation solutions or impregnated with the reagents without tearing because of their low wet strength, this can easily be carried out with polyvinyl alcohol or polyvinyl alcohol/polyvinyl acetate coated glass fibre pads. In order to achieve an impregnation of polyvinyl alcohol or polyvinyl alcohol/polyvinyl acetate coated glass fibre pads with an erythrocyte-aggregating substance which is as homogenous as possible, such pretreated glass fibre pads can therefore advantageously be impregnated by immersion in a solution of the substance to be applied.

Any liquid can be chosen as the solvent which dissolves the substance which aggregates erythrocytes to an adequate extent, which does not have a negative influence on the properties of this substance and which, after impregnation of the glass fibre pad coated with polyvinyl alcohol or polyvinyl alcohol/polyvinyl acetate with the erythrocyte-aggregating substance, can be removed again in such a way that the plasma-separating properties of the filter material produced in this way are not impaired. In the majority of cases water or an aqueous buffer solution is the solvent of choice.

A drying step follows the impregnation process if the solvent for the erythrocyte-aggregating substance has to be removed separately. This is routinely the case if water is used as the solvent. In this case it must be decided at which temperature the drying process is carried out and how long it should take depending on the erythrocyte-aggregating substance. As a rule the temperatures are between 40° and 90° C. and the drying period is between 1 and 10 minutes.

For an application according to the present invention the concentration of the erythrocyte-aggregating substance on the surface of glass fibre layers treated with polyvinyl alcohol or polyvinyl alcohol/polyvinyl acetate is dependent on the type of the respective substance which has an aggregating effect and the amounts of blood from which it is intended to isolate the plasma. It must in any case be high enough to enable complete separation of plasma but it must not, however, be so high that interfering haemolysis occurs. This can be determined by simple experiments in which blood is applied to glass fibre layers impregnated with different concentrations of erythrocyte-aggregating substances and the plasma which passes through this layer by gravity and/or capillary force is investigated for whether it contains erythrocytes or haemoglobin. Such experiments can be carried out in a manner analogous to that provided in Example 2. The number of positive charges per gram of coated glass fibre layer has proven to be usable for characterizing the concentration of cationic polymers used. The amount according to the present invention is $10^{18}$ to $10^{21}$ charges per gram, preferably $5 \times 10^{19}$ to $10^{21}$ charges per gram.

A device according to the present invention for separating plasma from whole blood can consist of glass fibres coated with polyvinyl alcohol or polyvinyl alcohol/polyvinyl acetate and carrying a cationic polymer which are loosely stacked or in the form of papers, pads or felts. They can, however, also be used in any desired form by being held by an outer structure. For example columns, nutsch filters or other suitable vessels filled with glass fibres treated appropriately can be used for this in order to isolate plasma from blood by simple passage without centrifugation.

In particular a device according to the present invention, above all a glass fibre pad whose glass fibres are coated with polyvinyl alcohol or polyvinyl alcohol/polyvinyl acetate and which carry an erythrocyte-aggregating substance, can be used in the field of plasma isolation in a test carrier for the determination of a component of blood having a plasma isolation and a test zone. Examples of possible arrangements of such test carriers are feasible in analogy to the agents described for example in EP-A-0 045 476, EP-A-0 239 002 or EP-A-0 133 895 which are referred to herewith.

In FIG. 1 a type of test carrier design which contains a plasma separation layer according to the present invention is shown as an example.

Figure 2A:
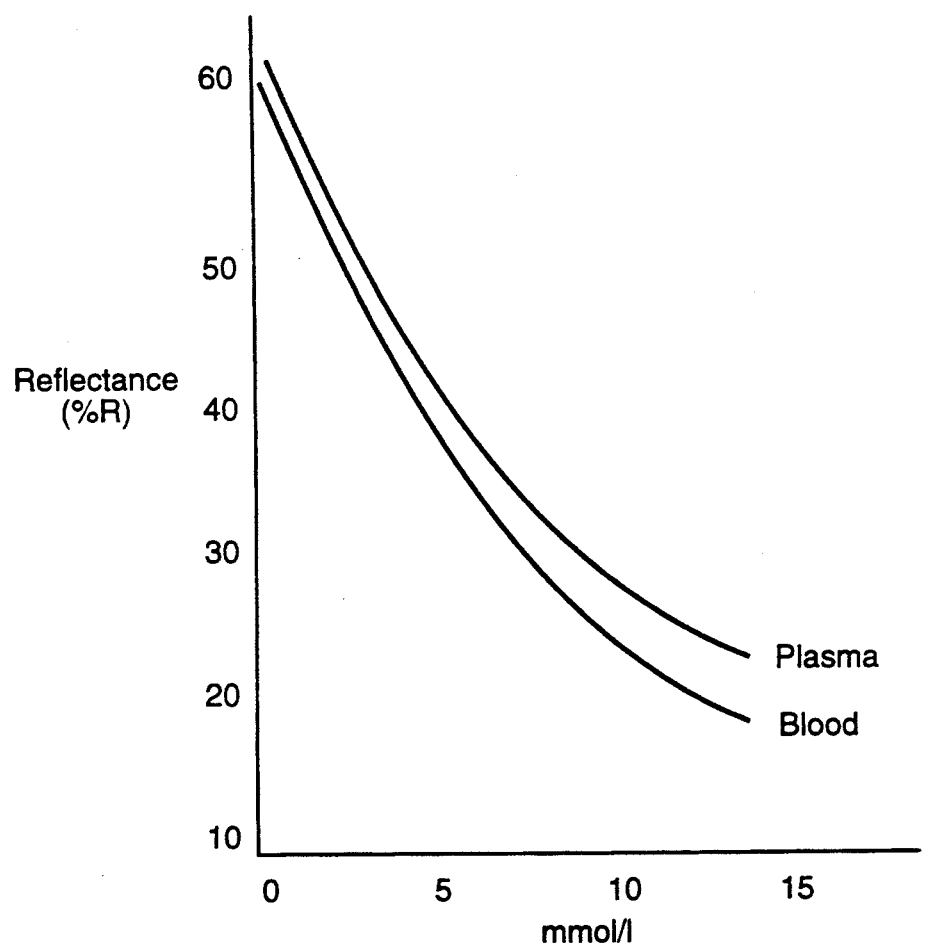

FIG. 2a shows function curves for the correlation of reflectance [%] and analyte concentration [mg/l] using a test carrier according to FIG. 1 with a separation layer for blood and plasma in sample liquids.

For FIG. 2a, a glass fibre pad was used with 2% polyvinyl alcohol according to EP-A-0 239 002 as the separation layer.

FIG. 1: A transport layer (2) which serves to transport the sample liquid from the sample application zone and plasma isolation zone (7) into the test zone (8) is fixed onto an inert carrier foil (5), for example a plastic foil. In principle all materials are suitable as the transport layer (2) which are able to transport the liquid to be examined from the sample application zone (7) into the test zone (8) and which in this process do not alter it in such a way that the analysis becomes impaired. It is particularly preferable to use a glass fibre pad as the transport layer (2). A plasma separating layer (3) according to the present invention partially covers the transport layer (2). A protective layer (4) is mounted over the separating layer (3) which is intended to prevent damage of the separating layer (3) during the sample application, for example with a pipette. A net of inert material, for example plastic, has proven reliable for this. The protective layer (4) and separating layer (3) are fixed onto the inert carrier foil (5). This can, for example, be carried out by means of a strip of hot-setting adhesive (6). A carrier foil consisting of transparent plastic with a film layer (1) which contains the reagents necessary for carrying out the determination is attached at the side of the transport layer (2). This is preferably effected by a glued joint (9) for example a strip of hot-setting adhesive. The film layer (1) is positioned so that it can be brought into contact with the transport layer (2) in such a way that liquid transfer is possible by pressing the transparent carrier foil in the direction of the inert carrier foil (5).

In order to carry out the determination of an analyte in blood the sample is applied to the protective layer (4). The blood penetrates into the separation layer (3), erythrocytes are aggregated and retained. The plasma obtained in this way is sucked into the test zone (8) by capillary forces. The plasma in the transport layer (2) is brought into contact with the reagent layer by pressure on the carrier foil with the reagent layer (1), liquid penetrates into the reagent layer and the determination reaction is triggered. In the case of a colorimetric reaction, the reaction is for example observed visually through the carrier foil of the film layer (1) or is measured by reflectance photometry on the basis of the colour formed in the reagent layer.

The advantages achieved by the invention are essentially that cellular components can be removed from whole blood without previous dilution and without an interfering haemolysis. In addition to the erythrocytes, essentially all other corpuscular components of blood such as leucocytes and thrombocytes can also be separated.

Since the plasma separation layer according to the present invention is very effective, one can rapidly isolate plasma even from small blood samples.

Since the plasma separation layer does not have interfering effects on the blood sample which contacts it, no blood/plasma difference will be established in the subsequent determination of plasma constituents i.e. corresponding values obtained from blood and plasma.

It is intended to elucidate the invention in more detail in the following examples.

EXAMPLE 1 a) Production of glass fibre pad
1000 l deionized water
2 kg glass fibres type 108 A (John Manville, USA)
0.04 kg polyvinyl alcohol, type Kuralon VPB 105-2 (Rohtex Textil GmbH, GFR) serve as starting materials.

An inclined-screen machine (Voith, Heidenheim, GFR) is used as the paper machine. The fibres suspended in the water are pumped onto an inclined screen. While the liquid flows off, or is sucked off by a vacuum, the fibres orientate themselves on the screen surface and are dried as a pad over a drying cylinder. The drying takes place at 125° C. until a final humidity of 0.5-1.5% by weight is achieved. 2 m/per minute is selected as the suction and production rate so that a material is formed with an area weight of 60 g/m$^2$ and a thickness of 0.45 mm.

b) Impregnation of the glass fibre pad with cationic polymer: The glass fibre pad is impregnated with a 0.7% solution of Polybren ® ( BASF, Ludwigshafen, GFR). The specific impregnation uptake is ca 370 ml/m$^2$. The glass fibre pad is dried in a moving-product drier at 80° C. at a rate of 1 m/per minute.

c) Impregnation of the glass fibre pad with antibodies:
The glass fibre pad is impregnated (impregnation uptake 370 ml/m$^2$) analogously to Example 1 b) with a solution of anti-erythrocyte antibodies (Dakopatts) in physiological saline (concentration 4 mg/ml). It is dried at 60° C. in a moving-product drier at a rate of 1 minute.

d) Impregnation of the glass fibre pad with lectin
The glass fibre pad is impregnated with a solution of lectin from Ricinus communis (RCA 120, Boehringer Mannheim GmbH, Mannheim, GFR) in phosphate-buffered (1.25 mmol/l) physiological saline (concentration 1 mg/ml) and dried analogously to Example 1 c).

e) Impregnation of the glass fibre pad with antibodies and cationic polymer
The glass fibre pad is impregnated with a solution of 0.7% Polybren ® and 1 mg/ml anti-erythrocyte antibodies (Dakopatts) in 10 mM Hepes buffer, pH 7.2 analogous to Example 1 c) and dried.

EXAMPLE 2

Plasma separation properties

The separation performance of the glass fibre pads according to the present invention produced in Example 1 is measured in a set-up in which the whole surface of a separation pad measuring 6×6 mm is placed at one end of a glass fibre pad which serves to transport plasma with 25 g/m$^2$ area weight (Binzer, GFR) and measuring 20×6 mm.

32 μl blood with a haematocrit of 48% is pipetted onto the separation pad and the erythrocyte front is measured after 2 minutes on the transport pad.

In addition the haemolysis caused by 2.2 mg separation pad with 1 dl blood is measured.

Glass fibre-containing layers according to the present invention are compared with plasma separation layers of the state of the art. The results are shown in Table I. Only the plasma separation layers according to the present invention separate erythrocytes very well without marked haemolysis.

TABLE 1

| Plasma separation layer | Erythrocyte front [mm] | Haemolysis [g Hb/dl] |
|---|---|---|
| Glass fibers without polyvinyl alcohol and without cationic polymer | 1–2 | 0.45 |
| Glass fibers with 2% polyvinyl alcohol | 2.8 | 0.05 |
| Glass fibers with Polybren ® | <0.2 | 0.3 |
| Glass fibers with 2% polyvinyl alcohol and Polymin P | <0.2 | 0.1 |
| Glass fibers with 2% polyvinyl alcohol and Polybren ® | <0.2 | 0.01 |
| Paper (Whatman 31 ET Chrom) with Polybren ® (acc. to EP-A-0 325 413) | no plasma separation | |
| Glass fibers with 2% polyvinyl alcohol and lectin | <0.2 | 0.01 |
| Glass fibers with 2% polyvinyl alcohol and antibodies | <0.2 | 0.01 |
| Glass fibers with 2% polyvinyl alcohol antibodies, and Polybren ® | <0.2 | no haemolysis measurable |

EXAMPLE 3

Blood/plasma difference when using a test carrier to detect potassium in blood and plasma.

Three plasma separation layers are produced and each is used as a layer (3) on a test carrier according to FIG. 1.

Plasma separation layers:
a) Glass fibres with 2% polyvinyl alcohol (according to EP-A-0 239 002, produced according to Example 1 a).
b) Glass fibres With 2% polyvinyl alcohol and cationic polymer (produced according to Example 1 b).

Each of the plasma separation layers are attached to a 150 mm long and 6 mm wide white polyester foil as a hot-setting adhesive strip under a 6×6 mm polyamide protective net and as described in Example 2 above a 20×6 mm glass fibre pad (25 g/m², Binzer, German Federal Republic).

A 15 mm long and 6 mm wide transparent polyester foil (200 μm thick) which is coated with the necessary reagents for the analyte determination is attached to the white polyester foil with a hot-setting adhesive strip as a reagent layer for the potassium test.

For the production of the reagent layer, a mixture of the following composition with a wet thickness of 300 μm is applied to the transparent polyester foil and dried:

| | |
|---|---|
| Vinylacetate-maleic acid dibutylester-copolymer (Mowilith ® 35/73, Hoechst AG, Frankfurt, GFR) | 14.7 g |
| 2.2-diphenyl-1-cyano-acrylic acid-ethylhexylester (Uvinul ® N539, BASF, Ludwigshafen, GFR) | 18.4 g |
| 4-(2,6-dibromo-4-nitro-phenylazo-)-2-octadecyloxy-naphthol-1 (produced according to Example 3 c) | 0.130 g |
| Valinomycin | 0.600 g |
| Diatomaceous earth (Celatom ® MW 25, Eagle-Picher, Cincinatti, USA) | 28.2 g |
| Butyl acetate | 50.7 g |

A second layer of the following composition having a wet film thickness of 150 μm is applied to this layer and also dried.

| | |
|---|---|
| Hydroxyethyl cellulose (Natrosol ® 250G, Hercules Inc., Willmington, Delaware, USA) in water | 41.5 g |
| N,N-bis-(hydroxyethyl)-aminoethanesulfonic acid | 8.5 g |
| Ethanol | 64 ml |
| adjusted to pH 7.8 with LiOH. | |

This reagent layer is combined with the test carrier as described above after dividing it into 15×6 mm pieces.

c) 4-[2,6-dibromo-4-nitrophenyl)azo]-2-octadecyloxy-1-naphthol ca) 2-octadecyloxynaphthalene 172.8 g (1.2 mol) 2-naphthol (98%) is added to a solution of 48 g (1.2 mol) sodium hydroxide (99%) in 1 l ethanol in a 4 l three-neck flask with stirrer, cooler and thermometer, after it has dissolved 417 g (1.25 mol) n-octadecylbromide are added and the reaction mixture is heated for 14 hours under reflux. After addition of a further 1 l ethanol the hot solution is aspirated over a Seitz filter to remove inorganic material and the weak pink coloured filtrate is brought to crystallization by placing it in an ice bath for 30 minutes. After aspiration of the almost colourless crystals, the filter cake is washed in portions with ca 700 ml ethanol and after drying over diphosphorus pentoxide 371.9 g (93.7% of the theoretical yield) 2-octadecyloxynaphthalene are obtained as colourless crystals, Fp 64°–68° C.

TLC: silica gel 60 (Merck), mobile solvent: n-heptane/methylene ketone 2:1, $R_f = 0.34$ cb) 2-octadecyloxy-1-naphthol 594 g (1.5 mol) 2-octadecyloxynaphthalene and 397 g (0.75 mol) lead tetraacetate are added to a mixture of 3 l glacial acetic acid and 600 ml acetic anhydride in a 10 l three-neck flask with stirrer, Claisen attachment, thermometer and cooler with a calcium chloride tube and it is heated to 55° C. Over a period of 4 days a further 400 g lead tetraacetate are added in portions (each of 100 g) at intervals of 24 hours while stirring. Afterwards the yellow solution which is formed is cooled to room temperature, stirred again for 30 minutes after addition of 1.5 l water, the crystal slurry which forms is aspirated and washed in portions with 2 l water. The wet crude product is dissolved in 4 l toluol and shaken three times with 1 l portions of water, three times with 1 l saturated sodium hydrogen carbonate solution and then again three times with 1 l water. After drying the toluol phase over sodium sulphate, aspiration and concentration by evaporation, 635 g brown crude product are obtained which is purified chromatographically as follows: the crystallizate obtained is dissolved in a mixture of 1.3 l toluol/isohexane 5:2 and the solution is applied to a silica gel 60 (Merck) column, inside diameter 11.5 cm, filling height 1.2 m. Toluol-/isohexane 5:2 is used as the mobile solvent and fractions of ca 300 ml are taken. Fractions 9–52 are combined and concentrated by evaporation until constancy of weight. One obtains 324.2 g 2- octadecyloxy-1-naphthol acetate, mp 67°-68° C. This is dissolved without further purification in 1.8 l methanol while heating and cooled to 20° C. 93 ml concentrated sulphuric acid are added dropwise to the suspension which formed within 15 minutes without cooling and while stirring, whereby the temperature increases to 35° C. Subsequently it is heated for 2 hours under reflux, then cooled with an ice bath and stirred for a further 30 minutes while cooling on ice. The crystals which form are aspirated, washed with 150 ml ice-cold methanol and dried at 35° C. in a drying cupboard over diphosphorus pentoxide. One obtains 294.4 g (47.5% of the theoretical yield) 2-octadecyloxy-1-naphthol, colourless crystals, Fp 58°-59° C.

cc) 4-[(2,6-dibromo-4-nitrophenyl)azo]-2-octadecyloxy-1-naphthol 22.7 g (0.33 mol) sodium nitrite are fed into 300 ml concentrated sulphuric acid in a 2 l three-neck flask with stirrer, Claisen attachment and thermometer during 10-15 minutes while stirring whereby the temperature of the reaction solution is allowed to increase to 35° C. It is then cooled to 20° C. and 230 ml glacial acetic acid are added dropwise in ca 15-20 minutes in such a way that the temperature is held at 20°-25° C. while cooling on ice. Afterwards 97.6 ml (0.33 mol) 2,6-dibromo-4-nitroaniline (Riedel de Haen [99%GC] are added in portions during 10 minutes while cooling occasionally whereby the temperature is kept at 19°- 21° C. and it is stirred again for a further 3 hours Afterwards this is poured into 3.5 l iced water and the diazonium salt solution which forms is added rapidly to a solution of 124 g (0.3 mol) 2-octadecyloxy-1-naphthol in a mixture of 3 l glacial acetic acid and 300 ml chloroform with addition of 180 g (1.33 mol) sodium acetatetrihydrate. (In the production of the solution of the naphtholether care must be taken that after it has been fed into glacial acetic acid-chloroform with addition of sodium acetate it is again cooled down to 20° C. after a temperature increase to ca. 45° C.) After stirring for 3 hours in the ice bath the crystal product which is formed is aspirated, the residue is washed three times with 500 ml water each time and dried in a drying cupboard at 40° C. The crude product—295.5 g light brown crystals—is purified chromatographically. The azo compound is dissolved in 1 l toluol/methylene chloride 2:5 and applied to a silica gel 60 (Merck) column with an inside diameter of 11.5 cm, filling height of 1.2 m and eluted with toluol/methylene chloride 2:5. Fractions of ca 70 ml are taken. The fractions 57-173 are combined and concentrated by evaporation. One obtains 134.2 g brown crystals. These are dissolved in 480 ml toluol at 80° C., cooled to 65° C. and 800 ml isohexane are added while stirring vigorously. This is allowed to cool to 20° C. while stirring, placed overnight in a refrigerator, the crystals which form are aspirated and the filter cake is washed twice with 300 ml ice-cold toluol/isohexane 1:1.3 and subsequently with 300 ml isohexane. Afterwards it is dried in a drying cupboard at 40° C. over diphosphorus pentoxide until constancy of weight. One obtains 119.9 g (55.5% of the theoretical yield) azo compound, light brown crystals, mp 102°-103° C. TLC, silica gel 60 (Merck), mobile solvent: toluol/methylene chloride 2:5, $R_f$=0.38 Transmission spectra at an acid or alkaline pH in o-nitrophenyloctylether yield $\lambda_{max}$ values of 454 or 672 nm.

In order to assess the blood/plasma difference, the same test carriers are used to investigate whole blood and plasma which is obtained from blood by centrifugation as usual. 30 μl sample are pipetted onto the protective net (4) and the respective test carrier is then inserted into the commercial reflectance photometer Reflotron ® (Boehringer Mannheim GmbH, Mannheim, German Federal Republic). In the reflectance photometer the reagent layer on the flap is brought into contact with the liquid in the transport layer and the reaction which takes place is measured by reflectance photometry.

The results are shown in FIG. 2 a. While a marked blood/plasma difference is observed when using a glass fibre pad of the state of the art, test carriers using plasma separation layers according to the present invention are suitable for the determination of analytes from blood as well as from plasma.

We claim:

1. A non-hemolyzing device useful in separating plasma or serum from whole blood, comprising a layer which contains (i) glass fibers coated with polyvinyl alcohol or polyvinyl alcohol/polyvinyl acetate, and (ii) an erythrocyte aggregating substance.

2. Method for separating plasma or serum from whole blood comprising contacting a whole blood sample to the plasma or blood separating layer device of claim 1 wherein erythrocytes are aggregated and retained therein essentially without hemolysis and wherein plasma is allowed to pass therethrough.

3. Device of claim 1, wherein said erythrocyte aggregating substance comprises a cationic polymer, a lectin, or an antibody.

4. Method for separating serum or plasma from whole blood comprising contacting a whole blood sample to the plasma or blood separating layer device of claim 2 wherein erythrocytes are aggregated and retained therein without hemolysis and plasma is allowed to pass therethrough.

5. Device of claim 3, wherein said cationic polymer is a copolymer of N,N,N', N'-tetramethyl-1,6-hexanediamine and 1,3-dibromopropane.

6. Device of claim 1, wherein said glass fibers have an average diameter of from 0.5 μm to 2.5 μm.

7. Device of claim 6, wherein said glass fibers have an average diameter of from 0.5 μm to 1.5 μm.

8. Device of claim 1, wherein said glass fibers have a density of from 0.1 g/cm$^3$ to 0.5 g/cm$^3$.

9. Device of claim 8, wherein said glass fibers have a density of from 0.2 g/cm$^3$ to 0.4 g/cm$^3$.

10. Device of claim 1, wherein said polyvinyl alcohol or polyvinyl alcohol/polyvinyl acetate is present in an amount ranging from 0.5-20% by weight of said glass fiber containing layer.

11. Device of claim 10, wherein said polyvinyl alcohol or polyvinyl alcohol/polyvinyl acetate is present in an amount ranging from 1.0-10% by weight of said glass fiber containing layer.

12. Test carrier useful in separating plasma or serum from whole blood comprising a first non-hemolyzing zone containing glass fibers coated with polyvinyl alcohol or polyvinyl alcohol/polyvinyl acetate and containing an erythrocyte aggregating substance, and a second, separate zone for reception of plasma.

13. Method for separating plasma or serum from whole blood comprising contacting a whole blood sample to the first zone of the test carrier of claim 12 wherein erythrocytes are aggregated and retained therein and plasma or serum passes therethrough into said second, separate zone.

14. Test carrier of claim 12, wherein said erythrocyte aggregating substance comprises a polymer, a lectin, or an antibody.

15. Method for separating plasma or serum from whole blood comprising contacting a whole blood sample to the first zone of the test carrier of claim 14 wherein erythrocytes are aggregated and retained therein and plasma or serum passes therethrough into said second, separate zone.

* * * * *